United States Patent [19]

Someya et al.

[11] Patent Number: 5,207,819
[45] Date of Patent: May 4, 1993

[54] PHENOXYPROPIONIC ACID ESTER DERIVATIVES

[75] Inventors: Sinzo Someya, Tokorozawa; Seigo Koura, Nerima; Mikio Ito, Tokuyama; Yoichi Kitamura, Sin-nan-yoo; Hiroyuki Watanabe, Sin-nan-yoo; Kenji Tsuzuki, Sin-nan-yoo, all of Japan

[73] Assignees: Agro-Kanesho Co., Ltd, Tokyo; Tosoh Corporation, Yamaguchi, both of Japan

[21] Appl. No.: 535,518

[22] Filed: Jun. 11, 1990

Related U.S. Application Data

[62] Division of Ser. No. 184,052, Apr. 20, 1988, Pat. No. 4,948,421.

[30] Foreign Application Priority Data

Apr. 20, 1987 [JP]  Japan .................................. 62-97043
Aug. 20, 1987 [JP]  Japan .................................. 62-207172
Oct. 23, 1987 [JP]  Japan .................................. 62-267110

[51] Int. Cl.⁵ .................... A01N 43/82; C07D 413/12
[52] U.S. Cl. ..................................... 504/235; 544/354; 546/268; 546/277; 546/283; 546/301; 546/302
[58] Field of Search ...................... 71/92, 94; 544/354; 546/283, 268

[56] References Cited

U.S. PATENT DOCUMENTS

| | | | |
|---|---|---|---|
| 4,133,675 | 1/1979 | Schurer et al. | 546/300 |
| 4,227,009 | 10/1980 | Koch et al. | 71/88 |
| 4,531,969 | 6/1985 | Nestler et al. | 546/150 |
| 4,948,421 | 8/1990 | Someya et al. | 71/94 |

FOREIGN PATENT DOCUMENTS

383613 8/1990 European Pat. Off. .
410758 1/1991 European Pat. Off. .
139579 6/1989 Japan .
230575 9/1989 Japan .
290672 11/1989 Japan .
304077 12/1990 Japan .

OTHER PUBLICATIONS

Nissan Chemical Industries, *Chemical Abstracts*, vol. 98, No. 198278 (1983).
Davis et al, *Chemical Abstracts*, vol. 112, No. 174081 (1989).

Primary Examiner—Robert T. Bond
Assistant Examiner—E. Bernhardt
Attorney, Agent, or Firm—Nixon & Vanderhye

[57] ABSTRACT

Disclosed is a novel compound of the formula [I]:

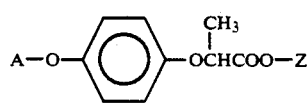

wherein A represents 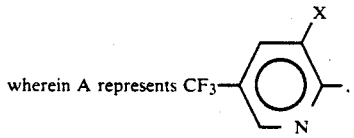

(wherein X is H or Cl)

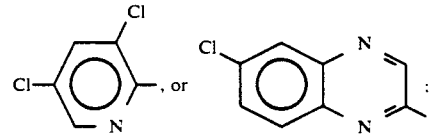

, or

Z represents 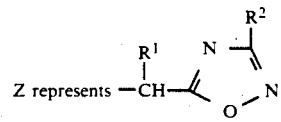

(wherein $R^1$ is H or $CH_3$, $R^2$ is H or $C_1$–$C_4$ alkyl), furylmethly group, tetrahydrofuryl group 2-tetrahydropyranylmethyl group or tetrahydrofurfuryl group which may be substituted with methyl group. The compound has strong herbicidal effect against the weeds belonging to the Family Gramineae.

2 Claims, No Drawings

PHENOXYPROPIONIC ACID ESTER DERIVATIVES

This is a division of application Ser. No. 07/184,052, filed Apr. 20, 1988, now U.S. Pat. No. 4,948,421.

BACKGROUND OF THE INVENTION

I. Field of the Invention

This invention relates to a novel compound, manufacturing process thereof and a herbicide composition comprising the same.

II. Description of the Related Art

A number of phenoxypropionic acid ester derivatives are known to have herbicidal activity. Examples of these derivatives include 2-[4-(4-trifluoromethylphenoxy)phenoxy]propionic acid methyl ester, 2-[4-(2,4-dichlorophenoxy)phenoxy]propionic acid methyl ester.

2-[4-(3,5-dichloro-2-pyridyloxy)phenoxy]propionic acid methyl ester and

2-[-4-(5-trifluoromethyl-2-pyridyloxy)phenoxy]propionic acid butyl ester.

However, these compounds are not satisfactory as herbicides in their effectiveness and selectivity. More particularly, when these ester derivatives are applied to the leaves and stems of weeds, it may take as long as 8 days to obtain the herbicidal effect of the derivatives.

SUMMARY OF THE INVENTION

Accordingly, the object of the present invention is to provide a novel compound which, when used as a herbicide, has satisfactory effectiveness and selectivity.

Another object of the present invention is to provide a herbicide composition which is effective for inhibiting the growth of weeds belonging to the Family Gramineae while not injuring the growth of broadleaved crops such as beet, bean, cotton, alfalfa, rapeseed, potato, sunflower, radish, Chinese cabbage, cabbage and tomato.

The present inventors have found that a specific phenoxypropionic acid ester derivative is effective for the inhibition of the growth of weeds belonging to the Family Gramineae, while harmless to the broadleaved crops to complete the present invention.

That is, the present invention provides a novel phenoxypropionic acid ester derivative of the formula [I]:

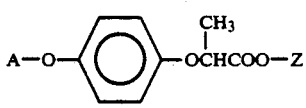

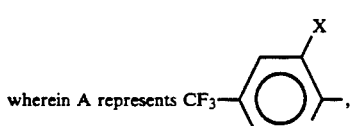

wherein A represents (wherein X is H or Cl)

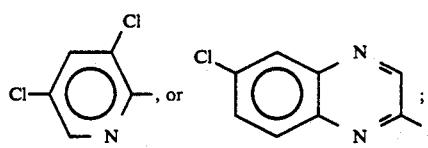

Z represents 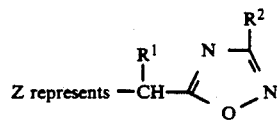

(wherein $R^1$ is H or $CH_3$, $R^2$ is $C_1$-$C_4$ alkyl), furylmethyl, tetrahydrofuryl 2-tetrahydropyranylmethyl or tetrahydrofurfuryl which may be unsubstituted or substituted with methyl group.

The present invention also provides a herbicide composition comprising herbicidal effective amount of the novel compound of the present invention in an agriculturally acceptable carrier.

By the present invention, a novel phenoxypropionic acid ester derivative was provided, which is useful as a herbicide with satisfactory effectiveness and selectivity. The novel compound of the present invention is very effective for inhibiting the growth of weeds, especially those belonging to the Family Gramineae. On the other hand, the compound of the present invention is harmless, when used in an appropriate herbicidal amount, to valuable broadleaved crops such as beans, cotton, carrot, potato, beet, cabbage, mustard, peanuts, radish, tobacco, tomato and cucumber. Thus, the compound of the present invention is excellent as an effective ingredient of a herbicide composition.

DETAILED DESCRIPTION OF THE PREFERRED EMBODIMENTS

A preferred example of the phenoxypropionic acid ester derivative of the present invention represented by the formula [I] described above include on which is represented by the following formula [II]:

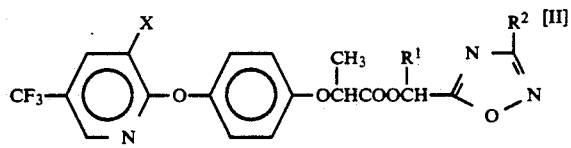

wherein X is H or Cl, $R^1$ is H or $CH_3$, and $R^2$ is $C_1$-$C_4$ alkyl. Specific preferred and non-limiting examples of the phenoxypropionic acid ester derivative of the formula [II] include those summarized in Table 1 below.

TABLE 1

| Compound No. | X | $R^1$ | $R^2$ |
|---|---|---|---|
| 1 | Cl | H | $CH_3$ |
| 2 | H | $CH_3$ | $CH_3$ |
| 3 | Cl | $CH_3$ | $CH_3$ |
| 4 | Cl | $CH_3$ | $C_2H_5$ |
| 5 | Cl | $CH_3$ | n-$C_3H_7$ |
| 6 | Cl | $CH_3$ | i-$C_3H_7$ |
| 7 | Cl | $CH_3$ | n-$C_4H_9$ |
| 8 | Cl | $CH_3$ | t-$C_4H_9$ |
| 9 | Cl | H | H |

The compound represented by the formula [II] may be racemic or a stereoisomer. In an especially preferred embodiment, the compound of the formula [II] has R-configuration with respect to the carbon atoms marked with "*" in the following formula [II']:

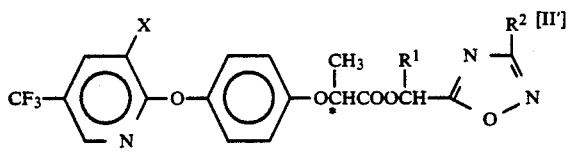

Preferred and non-limiting specific examples of the R enantiomer represented by the formula [II'] include those shown in Table 2 below.

TABLE 2

| Compound No. | X  | $R^1$ | $R^2$ |
|---|---|---|---|
| 10 | Cl | $CH_3$ | $CH_3$ |
| 11 | Cl | H | $CH_3$ |

Another group of preferred examples of the compound represented by the formula [I] is expressed by the following formula [III]:

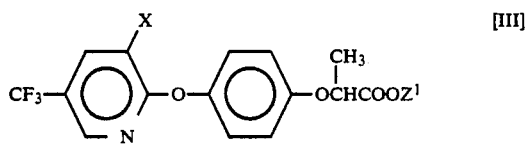

wherein $Z^1$ represents furylmethyl, tetrahydrofuryl 2-tetrahydropyranylmethyl or tetrahydrofurfuryl which may be unsubstituted or substituted with methyl.

Preferred and non-limiting examples of the compound represented by the formula [III] include those summarized in Table 3 below.

TABLE 3

| Compound No. | X | $Z^1$ |
|---|---|---|
| 12 | Cl | —CH₂—(tetrahydrofuryl) |
| 13 | H | —CH₂—(tetrahydrofuryl) |
| 14 | Cl | (tetrahydrofuryl) |
| 15 | Cl | —CH₂—(furyl) |
| 16 | Cl | —CH₂—(tetrahydropyranyl) |
| 17 | Cl | —CH₂—(methyl-tetrahydrofuryl) |

The compound by the formula [II] may be racemic or stereoisomer. In an especially preferred embodiment, the compound represented by the formula [III] has R-configuration with respect to the carbon atom marked with "*" in the following formula [III']:

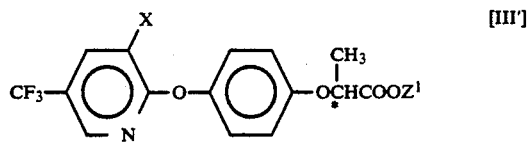

Specific examples of the R-enantiomer represented by the formula [III'] include the R-enantiomer of the compound No. 12 (the R-enantiomer is hereinafter referred to as compound No. 18).

Still another group of the preferred examples of the compound of formula [I] is represented by the following formula [IV]:

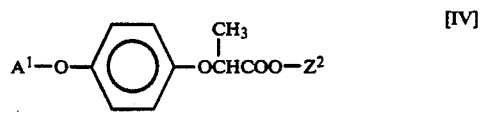

wherein $A^1$ represents

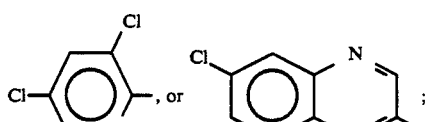

(wherein $R^1$ is H or $CH_3$, $R^2$ is $C_1$–$C_4$ alkyl), or tetrahydrofuryl.

Preferred and non-limiting examples of the compound represented by the formula [IV] include those summarized in Table 4 below.

TABLE 4

| Compound No. | $A^1$ | $Z^2$ |
|---|---|---|
| 19 | (3-Cl, 5-Cl pyridyl) | —CH(CH₃)—(dimethyl-oxazoline) |
| 20 | (chloroquinoxalinyl) | —CH(CH₃)—(methyl-oxazoline) |
| 21 | (chloroquinoxalinyl) | —CH₂—(tetrahydrofuryl) |
| 22 | (3-Cl, 5-Cl pyridyl) | —CH₂—(tetrahydrofuryl) |

The phenoxypropionic acid ester derivative represented by the formula [I] may be prepared in accordance with one of the following equations (i) to (iii). In the following equations, Hal means halogen, and A and Z represent the same meaning as in formula [I].

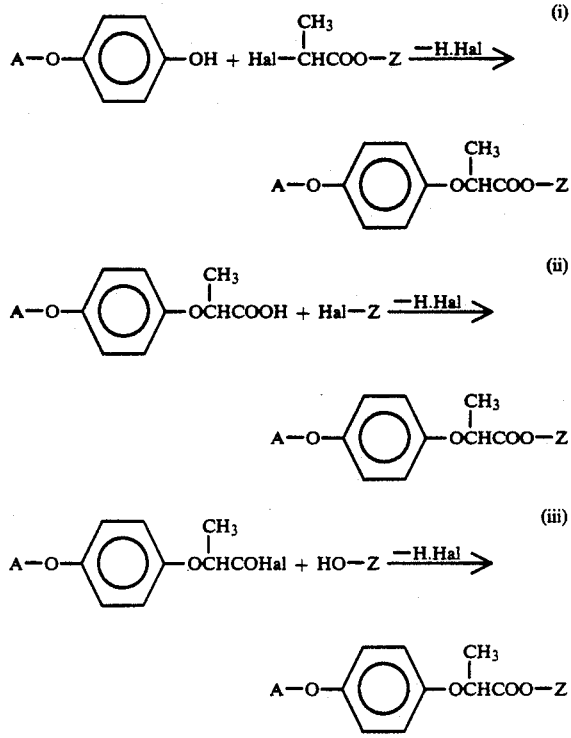

These reactions may be accomplished in the presence of a base. Preferred examples of the base which may be employed in these reactions may include tertiary amines such as triethylamine, pyridine, 1,8-diazabicyclo[5,4,-0]undec-7-ene and dimethylaniline; alkali metal hydroxide such as sodium hydroxide; alkaline earth metal hydroxides such as calcium hydroxide; alkaline metal salts of carbonic acid such as sodium carbonate, potassium carbonate, sodium hydrogen carbonate and potassium hydrogen carbonate; and metal hydrides such as sodium hydride. The concentration of the base in the reaction system may preferably be one to ten equivalents with respect to the reactant containing the group "A".

The reactions may be carried out with or without a solvent. Preferred examples of the solvents which may be employed in the reactions include ketones such as acetone and methyl ethyl ketone; aromatic hydrocarbons such as benzene and xylene; ethers such as ethyl ether, tetrahydrofuran and dioxane; halogenated hydrocarbons such as chlorobenzene, chloroform, tetrachloromethane and dichloroethane; tertiary amines such as triethylamine, pyridine and dimethylaniline; and polar solvents such as hexamethylphosphoramide.

The reactions may be carried out at a temperature ranging from 0° C. to 150° C., preferably 20° C. to 100° C. The reactions may be completed in from several minutes to about 48 hours.

The R-enantiomers of the formulae [II'] and [III'] may be obtained by using corresponding starting materials which are R-enantiomers. The R-enantiomers which can be employed as the starting materials are well-known. R-enantiomers of the present invention may also be obtained by conventional racemic resolution.

The present invention also provides a herbicide composition comprising as an effective ingredient the novel phenoxypropionic acid derivative of the present invention in the amount effective for exhibiting the herbicidal effect in an agriculturally acceptable carrier. The agriculturally acceptable carriers per se are well-known in the art, and either liquid carrier or solid carrier may be employed. Preferred examples of the liquid carrier or diluent may include water, hydrocarbons, ethers, alkoxy alcohols, ketones, esters, amides and sulfoxides. Preferred examples of the solid carriers or extender may include powder and granules of inorganic materials such as slaked lime, gypsum, calcium carbonate, silica, pearlite, pumice, diatomaceous earth, alumina, zeolite and clay minerals (e.g., talc, vermiculite and kaolinite); powder and granules of plant products such as starch, cereals and glucose; and powder and granules of synthetic products such as phenol resins, carbon resins and vinyl chloride resins. The concentration of the active compound in the composition is not critical and may usually be 0.1% by weight to 90% by weight, preferably 1% by weight to 80% by weight.

If necessary, the herbicide composition of the present invention may contain a surfactant. The surfactants are well-known and widely used in the art. Preferred examples of the surfactants include anion surfactants such as alkylsulfate esters, arylsulfonic acids, salts or succinic acid and polyethyleneglycoalkylaryl ethers and ester salts of sulfuric acid; cation surfactants such as alkylamines and polyoxyethylenealkylamines; non-ionic surfactants such as polyoxyethyleneglycol ethers and polyol esters; and ampholytic surfactants. If desired, the composition of the present invention may contain other additives which are often employed in herbicide compositions. The examples of such additives may include stabilizers, dispersion stabilizers, fixing agents, effective prolongers and synergists.

The herbicide composition may be formulated to an emulsiable concentrate, wettable powder, aqueous solution, oily solution, granule or powder. The methods of formulating herbicide compositions are well-known in the art.

If desired, the herbicide composition of the present invention may contain other agricultural chemicals such as pesticides, fungicides, herbicides and plant growth regulators, as well as fertilizers. In some cases, it may be preferred to blend the following herbicides to reduce the labor of application or to widen the range of the weeds which can be controlled by the composition. Examples of such herbicides may include
2,4-dichlorophenoxy acetic acid, as well as salts, esters and alkylesters thereof;
2-methyl-4-chlorophenoxy acetic acid, as well as salts and esters thereof;
2-methyl-4-chlorophenoxy acetic acid, as well as salts and esters thereof;
d,1,2-(4-chloro-O-tolyloxy)propionic acid, as well as salts and esters thereof;
4-cyano-2,6-diiodophenyl octanoate;
2,4-dichlorophenyl-4'-nitrophenyl ether;
2,4,6-trichlorphenyl-4'-nitrophenyl ether;
2,4-dichlorophenyl-3'-methoxy-4'-nitrophenyl ether;
methyl 3,4-dichlorocarbanilidate;
iospropyl 3-chlorocarbanilidate;
S-4-chlorobenzyl diethylthiocarbamidate;
4-nitrophenyl-3',5'-xylxyl ether;
S-ethyl hexahydro-1H-azepin-1-carbothioate; 3,4-dichlorpropion anilide;
2-chloro-2',6'-diethyl-N-(butoxymethyl)acetanilide;

2-chloro-2',6'-diethyl-N-(butoxyethyl)acetoanilide;
1-(α,α-dimethylbenzyl)-3-p-tolyl urea;
2,4-bis(acetylamino)-6-methylthio-1,3,5-triazine;
2-ethylamino-4-isopropylamino-6-methylthio-1,3,5triazine;
2,4-bis(isopropylamino)-6-methylthio-1,3,5-triazine;
5-tert-butyl-3-(2,4-dichloro-5-isopropoxyphenyl)-1,3,4-oxadiazoline-2-one; 2,6-dichlorobenzonitrile;
2,6-dichlorothiobenzamide;
2-amino-3-chloro-1,4-naphthoquinone;
2,4-dichlorophenyl-3'-carbomethoxy-4'-nitrophenyl ether;
N-p-chlorobenzyloxyphenyl-3,4,5,6-tetrahydrophthalimide;
2,4-dichlorophenyl-3'-ethoxyethoxy-4'-nitrophenyl ether;
N-(1-ethylpropyl)-2,6-dinitro-3,4-xylidine;
4-(2,4-dichlorobenzoyl)-1,3-dimethyl-pyrazole-5-yl-p-toluene sulfonate;
4-(2,4-dichlorobenzoyl)-1,3-dimethyl-5-(benzoylmethoxy)pyrazole;
4-(2,4-dichloro-3-methylbenzoyl)-1,3-dimethyl-5-(benzoylmethoxy)pyrazole;
O,O-diisopropyl-2-(benzenesulfonamide)-ethylenedithiophosphate;
3,3'-diemthyl-4-methoxybenzophenone;
α-(2-naphthoxy)-propionanilide;
O-ethyl-O-(3-methyl-6-nitrophenyl)-N-sec-butylphosphorothioamidate;
3-isopropyl-2,1,3-benzothiazinone-(4)-2,2-dioxide and salts thereof; and
S-(2-methyl-1-piperidyl-carbonylmethyl)-O,O-di-n-propyldithiophosphate;
S-benzyl-N,N-dimethylthiocarbamate.

Specific non-limiting examples of the preferred compositions of the present invention will now be described. In the following examples, all parts are based on weight.

| Composition 1 (Emulsifiable Concentrate) | |
|---|---|
| Compound of the present invention: | 20 parts |
| xylene: | 60 parts |
| Solpol (a surfactant commercially available from Toho Kagaku Kogyo) | 20 parts |

This composition may be prepared by uniformly mixing the components.

| Composition 2 (Wettable Powder) | |
|---|---|
| Compound of the present invention: | 20 parts |
| White Carbon: | 10 parts |
| Zeaklite: | 65 parts |
| Solpol (a surfactant commercially available from Toho Kagaku Kogyo) | 5 parts |

This composition may be prepared by mixing and pulverizing the components.

The herbicide composition of the present invention is useful for inhibiting the growth of weeds, especially those belonging to the Family Gramineae such as those belonging to the genera Digitaria, Echinocholoa, Avena, Oryza, Triticum, Zea and Setaria. Specific examples of the plants of which growth may be inhibited by the herbicide composition of the present invention may include large crabgrass, barnyardgrass, annual bluegrass, Johnson grass, wild oats, goosegrass, green foxtail, yellow foxtail, quack grass and Bermudagrass.

On the other hand, the herbicide composition of the present invention is substantially harmless to broad-leaved crops such as beans, cotton, carrot, potato, beet, cabbage, mustard, peanuts, radish, tobacco, tomate, rapeseed, Chinese cabbage, alfalfa and cucumber. Thus, the herbicide composition of the present invention is useful for the cultivation of the above-mentioned broad-leaved crops.

The amount of the compound of the present invention to be applied to the field varies depending on the formulation of the composition, method of application, species and stage of growth of the weeds. In usual, the amount to be spinkled may be 0.0005–10 kg/ha, preferably 0.1–1 kg/ha in terms of the effective ingredient of the present invention.

The herbicide composition of the present invention may directly be applied to the leaves or stems of weeds or to the field before the germination of the weeds. The herbicide composition may be applied as it is or may be diluted with water before use.

The invention will now be described by way of the examples thereof. It should be understood that the examples are presented for the illustration purpose only and should not be interpreted any restrictive way.

EXAMPLE 1

Preparation of Compound No. 1

To 50 ml of acetonitrile, were added 1.83 g of 2-[4-(3-chloro-5-trifluoromethyl-2-pyridyloxy)-phenoxy] propionic acid, 0.8 g of 3-methyl-5-chloromethyl-1,2,4-oxadiazol and 0.83 g of anhydrous potassium carbonate, and the mixture was heated to reflux under stirring for 16 hours. After cooling the mixture, inorganic materials were removed by filtration and the acetonitrile was evaporated. The residue was purified by a column chromatography (silica gel, eluant: benzene/ethyl acetate=10/1 (v/v) to obtain 1.23 g of the desired product (compound No. 1).

Refraction Index $n_D = 1.5250$.

$^1$NMR spectrum (CDCl$_3$, ppm): 1.62 (3H, d), 2.31 (3H, s), 4.83 (1H, q), 5.28 (2H, s), 6.88 (4H, mc), 7.82 (1H, d), 8.10 (1H, d).

EXAMPLE 2

Preparation of Compound No. 2

The same procedure as in Example 1 was repeated except that 0.8 g of 2-[4-(5-trifluoromethyl-2-pyridyloxy)-phenoxy]propionic acid, 0.39 g of 3-methyl-5(α-chloroethyl)-1,2,4-oxadiazole and 0.37 g of anhydrous potassium carbonate were employed as the reactants to obtain 0.59 g of the desired product (compound No. 2).

Refraction Index $n_D^{25} = 1.5090$.

$^1$NMR spectrum (CDCl$_3$, δ ppm): 1.56 (3H, d), 1.62 (3H, d), 2.27 (3H, s), 4.75 (1H, q), 5.97 (1H, q), 6.88 (4H, mc), 7.68 (1H, d), 7.83 (1H, d), 8.32 (1H, d).

EXAMPLE 3

Preparation of Compound No. 3

The same procedure as in Example 1 was repeated except that 1.1 g of 2-[4-(3-chloro-5-trifluoromethyl-2-pyridyloxy)-phenoxyl]propionic acid, 0.44 g of 3-methyl-5-(α-chloroethyl)-1,2,4-oxadiazole and 0.42 g of anhydrous potassium carbonate were employed as the reactants to obtain 0.8 g of the desired product (compound No. 3).

Refraction Index $n_D^{25} = 1.6150$.

$^1$H-NMR spectrum (CDCl$_3$, δ ppm): 1.67 (6H, d), 2.38 (3H, s), 4.85 (1H, g), 6.08 (1H, q), 7.00 (4H, mc), 7.92 (1H, d), 8.22 (1H, d).

EXAMPLE 4

Preparation of Compound No. 4

The same procedure as in Example 1 was repeated except that 1.8 g of 2-[4-(3-chloro-5-trifluoromethyl-2-pyridyloxy)-phenoxy]propionic acid, 0.97 g of 3-ethyl-5-(α-chloroethyl)-1,2,4-oxadiazole and 0.82 g of anhydrous potassium carbonate were employed as the reactants to obtain 1.68 g of the desired product (compound No. 4).

Refraction Index $n_D^{25}$ = 1.5122.

$^1$H-NMR spectrum (CDCl$_3$, δ ppm): 1.32 (3H, t), 1.70 (3H, d), 1.73 (3H, d), 2.76 (2H, q), 4.86 (1H, q), 6.03 (1H, q), 6.94 (4H, mc), 7.85 (1H, d), 8.14 (1H, d).

EXAMPLE 5

Preparation of Compound No. 5

The same procedure as in Example 1 was repeated except that 1.82 g of 2-[4-(3-chloro-5-trifluoromethyl-2-pyridyloxy)-phenoxy]-propionic acid, 1.05 g of 3-n-propyl-5-(α-chloroethyl)-1,2,4-oxadiazole and 0.82 g of anhydrous potassium carbonate were employed as the reactants to obtain 1.13 g of the desired product (compound No. 5).

Refraction Index $n_D^{25}$ = 1.5086.

$^1$H-NMR spectrum (CDCl$_3$, δ ppm): 1.11 (3H, t), 1.71 (8H, mc), 2.68 (2H, t), 4.80 (1H, q), 5.98 (1H, q), 6.88 (4H, mc), 7.79 (1H, d), 8.08 (1H, d).

EXAMPLE 6

Preparation of Compound No. 6

The same procedure as in Example 1 was repeated except that 1.82 g of 2-[4-(3-chloro-5-trifluoromethyl-2-pyridyloxy)-phenoxy]propionic acid, 1.05 g of 3-isopropyl-5-(α-chloroethyl)-1,2,4-oxadiazole and 0.82 g of anhydrous potassium carbonate were employed as the reactants to obtain 1.31 g of the desired product (compound No. 6).

Refraction Index $n_D^{25}$ = 1.5040.

$^1$H-NMR spectrum (CDCl$_3$, δ ppm):
1.41 (6H, d), 1.75 (3H, d), 1.77 (3H, d), 3.17 (1H, h), 4.90 (1H, q), 6.08 (1H, q), 7.00 (4H, mc), 7.90 (1H, d), 8.20 (1H, d).

EXAMPLE 7

Preparation of Compound No. 7

The same procedure as in Example 1 was repeated except that 1.82 g of 2-[4-(3-chloro-5-trifluoromethyl-2-pyridyloxy)-phenoxy]propionic acid, 1.13 g of 3-n-butyl-5-(α-chloroethyl)-1,2,4-oxadiazole and 0.82 g of anhydrous potassium carbonate were employed as the reactants to obtain 1.14 g of the desired product (compound No. 7).

Refraction Index $n_D^{25}$ = 1.5108.

$^1$H-NMR spectrum (CDCl$_3$, δ ppm): 1.10 (3H, t,), 1.66 (10H, mc), 2.71 (2H, t), 4.79 (1H, q), 5.98 (1H, q), 6.88 (4H, mc), 7.80 (1H, d), 8.09 (1H, d).

EXAMPLE 8

Preparation of Compound No. 8

The same procedure as in Example 1 was repeated except that 1.8 g of 2-[4-(3-chloro-5-trifluoromethyl-2-pyridyloxy)-phenoxy]propionic acid, 1.13 g of 3-t-butyl-5-(α-chloroethyl)-1,2,4-oxadiazole and 0.82 g of anhydrous potassium carbonate were employed as the reactants to obtain 1.16 g of the desired produce (compound No. 8).

Refraction Index $n_D^{25}$ = 1.5074.

$^1$H-NMR spectrum (CDCl$_3$, δ ppm): 1.37 (9H, s), 1.70 (3H, d), 1.73 (3H, d), 4.88 (1H, q), 6.10 (1H, q), 6.90 (4H, mc), 7.80 (1H, d), 8.13 (1H, d).

EXAMPLE 9

Preparation of Compound No. 9

The same procedure as in Example 1 was repeated except that 0.9 g of 2-[4-(3-chloro-5-trifluoromethyl-2-pyridyloxy)-phenoxy]propionic acid, 0.36 g of 5-(α-chloromethyl)-1,2,4-oxadiazole and 0.42 g of anhydrous potassium carbonate were employed as the reactants to obtain 0.35 g of the desired product (compound No. 9).

Refraction Index $n_D^{25}$ 1.5255.

$^1$H-NMR spectrum (CDCl$_3$, δ ppm): 1.64 (3H, d), 4.83 (1H, q), 5.30 (2H, s), 6.85 (4H, mc), 7.79 (1H, d), 8.12 (1H, d), 8.30 (1H, s).

EXAMPLE 10

Test for Evaluation of Effectiveness in Growth Inhibition by Treatment of Leaves and Stems Field soil was packed in a plastic vat sizing 22 cm × 16 cm and seeds of soybean (*Glycine max*), rice (*Oryza sativa*), wheat (*Triticum aestivum*), corn (*Zea mays*), and oats (*Avena fatua*) were sown. The field soil was covered with soil of 1 cm thickness which contains seeds of weeds, i.e., large crabgrass (*Digitaria adscendens*), barnyardgrass (*Echinochloa crus-galli*), polygonum (*Polygonum blumei*), chickweed (*Stellaria neglecta*) and common lambsquarters (*Chenopodium album*). When the plants belonging to the Family Gramineae grew to have 3.0–3.5 leaves, each of the compound Nos. 1–9 was applied to the leaves and stems of the plants in the amount of 0.125, 0.0625 or 0.03125 kg/ha.

After 14 days from the application of the herbicide, the conditions of the growth of the weeds were observed, and the degree of the growth inhibition was evaluated. The degree of growth inhibition was rated in 5 ranks according to the ineffectiveness of the compound, i.e., rank 1 to rank 5, wherein rank 5 means that all plants completely died. The results are shown in Table 5 below.

TABLE 5

| Compound No. | Amount Treated (kg/ha) | large crabgrass | barnyard-grass | oats | poly-gonum | chick-weed | common lambs-quaters | soy-bean | beet | rice | wheat | corn |
|---|---|---|---|---|---|---|---|---|---|---|---|---|
| 1 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 4 | 4 | 5 |
|   | 0.03125 | 4–5 | 5 | 5 | 1 | 1 | 1 | 1 | 1 | 3 | 3 | 4 |
| 2 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 5 | 5 | 4–5 |
|   | 0.03125 | 4–5 | 5 | 4–5 | 1 | 1 | 1 | 1 | 1 | 4 | 4 | 4 |

TABLE 5-continued

| Compound No. | Amount Treated (kg/ha) | large crabgrass | barnyard-grass | oats | poly-gonum | chick-weed | common lambs-quaters | soy-bean | beet | rice | wheat | corn |
|---|---|---|---|---|---|---|---|---|---|---|---|---|
| 3 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 5 | 5 | 5 |
|   | 0.03125 | 5 | 5 | 5 | 1 | 1 | 1 | 1 | 1 | 4 | 5 | 4–5 |
| 4 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 4 | 5 | 5 |
|   | 0.03125 | 4–5 | 5 | 5 | 1 | 1 | 1 | 1 | 1 | 4 | 4–5 | 4–5 |
| 5 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 5 | 5 | 5 |
|   | 0.03125 | 5 | 5 | 5 | 1 | 1 | 1 | 1 | 1 | 4 | 4 | 5 |
| 6 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 4 | 5 | 5 |
|   | 0.03125 | 5 | 5 | 5 | 1 | 1 | 1 | 1 | 1 | 4 | 4–5 | 5 |
| 7 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 4 | 5 | 5 |
|   | 0.03125 | 5 | 5 | 5 | 1 | 1 | 1 | 1 | 1 | 3 | 4 | 5 |
| 8 | 0.125 | 5 | 5 | 5 | 1 | 1 | 1 | 1 | 1 | 4 | 5 | 5 |
|   | 0.0625 | 5 | 5 | 5 | 1 | 1 | 1 | 1 | 1 | 4 | 4 | 5 |
|   | 0.03125 | 4–5 | 5 | 5 | 1 | 1 | 1 | 1 | 1 | 3 | 4 | 4–5 |
| 9 | 0.125 | 5 | 5 | 5 | 1 | 1 | 1 | 1 | 1 | 5 | 5 | 5 |
|   | 0.0625 | 5 | 5 | 5 | 1 | 1 | 1 | 1 | 1 | 4 | 5 | 5 |
|   | 0.03125 | 4–5 | 5 | 5 | 1 | 1 | 1 | 1 | 1 | 4 | 4 | 5 |

It can be seen from Table 5 that the compound of the present invention is very effective for inhibiting the growth of the plants belonging to the Family Gramineae and harmless to the broadleaved crops.

EXAMPLE 11

Preparation of Compound No. 10

In 30 ml of dichloromethane, 1.67 g of 3-methyl-5-hydroxymethyl-1,2,4-oxadiazole was added. To this mixture, was added dropwise 4.97 g of R-(+)-2-[4-(3-chloro-5-trifluoromethyl-2-pyridyloxy)phenoxy]propionyl chloride in 10 ml of dichloromethane. After stirring the mixture for 10 minutes at room temperature, 1.32 g of triethylamine was added and the resulting mixture was stirred for 2 hours at room temperature. To the thus obtained reaction mixture, water was added and dichloroethane solution was separated, washed with water, dried over anhydrous magnesium sulfate and evaporated to remove the solvent. The residue was purified by column chromatography [silica gel, eluant: benzene/ethyl acetate = 10/1 (v/v)] to obtain 3.77 of the desired product (compound No. 10).

Specific Rotation $[\alpha]_D^{20} = +26.9°$ (c=1, CHCl$_3$).

$^1$H-NMR Spectrum (CDCl$_3$, δ ppm): 1.65 (3H, d), 1.70 (3H, d), 2.35 (3H, s), 4.80 (1H, q), 6.02 (1H, q), 6.91 (4H, mc), 7.83 (1H, d), 8.12 (1H, d).

The R-(+)-2-[4-(3-chloro-5-trifluoromethyl-2-pyridyloxy)-phenoxy]propionyl chloride used in the above example was prepared using R-(+)-2-(4-hydroxyphenoxy)propionic acid as a starting material via R-(+)-2-[4-(3-chloro-5-trifluoromethyl-2-pyridyloxy)-phenoxy]propionic acid as follows:

To a solution of 3.52 g of sodium hydroxide in 15 ml of water, 9.8 g of S-(−)-2-chloropropionic acid methyl ester was added dropwise at 40° C. Thereafter, water and methanol were evaporated under reduced pressure to obtain an aqueous solution of Sodium-(−)-2-chloro propionate. This aqueous solution was added dropwise to a mixture of 9.6 g of sodium hydroxide, 13.7 ml of water and 11 g of hydroquinone under nitrogen atmosphere at room temperature for 1 hour. Then the resulting mixture as allowed to react at 40° C. for 5 hours. To the mixture, 18 g of concentrated hydrochloric acid was added and then 40 g of methyl isobutyl ketone, 15 ml of water and 1 g of sodium hydrogen carbonate were added. Then the aqueous layer and the organic layer of the mixture was separated. The aqueous layer was acidified with concentrated hydrochloric acid and then R-(+)-2-(4-hydroxyphenoxy)propionic acid was extracted with methyl isobutyl ketone, and the solvent was evaporated under reduced pressure from the organic layer of the extract to obtain crystals. The crystals were washed once with 50 ml of benzene to obtain 6.2 g of R-(+)-2-(4-hydroxyphenoxy)propionic acid.

Specific Rotation $[\alpha]_D^{20} = +60.4°$ (c=1, acetone).

Preparation of
R-(+)-2-[4-(3-chloro-5-trifluoromethyl-2-pyridyloxy)-phenoxy]propionic acid In 200 ml of diemthylsulfoxide, 13 g of R-(+)-2-(4-hydroxyphenoxy)propionic acid and 9.45 g of potassium hydroxide powder were dissolved under nitrogen atmosphere. To this mixture, was added dropwise 15.5 g of 2,3-dichloro-5-trifluoromethyl pyridine at room temperature, and the resulting mixture was stirred at 70° C. for 15 hours. The thus obtained reaction mixture was poured into 1000 ml of water, followed by acidification with concentrated hydrochloric acid and by extraction with ether. The ether layer was dried over anhydrous magnesium sulfate and evaporated the solvent to obtain 20.9 g of R-(+)-2-[4-(3-chloro-5-trifluoromethyl-2-pyridyloxy)phenoxy]propionic acid.

Preparation of
R-(+)-2-[4-(3-chloro-5-trifluoromethyl-2-pyridyloxy)-phenoxy]propyonyl chloride In 20 ml of thionyl chloride, 3.3 g of R-(+)-2-[4-(3-chloride-5-trifluoromethyl-2-pyridyloxy)phenoxy]propionic acid was dissolved and the solution was heated to reflux for 4 hours to complete the reaction. Then excessive thionyl chloride was evaporated under reduced pressure to obtain 3.45 g of R-(+)-2-[4-(3-chloro-5-trifluoromethyl-2-pyridyloxy)phenoxy] propionyl chloride.

EXAMPLE 12

Preparation of Compound No. 11

In 30 ml of dichloromethane, 1.03 g of 3-methyl-5-(α-hydroxyethyl)-1,2,4-oxadiazole was dissolved. To this solution, a solution of 3.42 g of R-(+)-2-[4-(3-chloro-5-trifluoromethyl-2-pyridyloxy)phenoxy]propionyl chloride in 10 ml of dichloromethane was added dropwise at room temperature. After stirring the resulting mixture at room temperature for 10 minutes, 0.92 g of triethylamine was added thereto and the resulting mixture was stirred at room temperature for 2 hours. To the thus obtained reaction mixture, water was added and dichloromethane layer was separated, washed with water, dried over anhydrous magnesium sulfate and evaporated to remove the solvent. The residue was purified by column chromatography [silica gel, eluant: benzene/ethyl acetate=10/1 (v/v)] to obtain the desired product (compound No. 11).

specific rotation $[\alpha]_D^{20} = +29.5$ (c=1, CHCl$_3$).

$^1$H-NMR Spectrum (CDCl$_3$, δ ppm) 1.68 (3H, d), 2.35 (3H, s), 4.92 (1H, q), 5.3 (2H, s), 6.98 (4H, mc), 7.91 (1H, d), 8.22 (1H, d).

EXAMPLE 13

Test for Evaluation of Effectiveness in Growth Inhibition by Treatment of Leaves and Stems In a vat with 100 cm$^2$ area, filed soil was placed and seeds of soybean, beet, oats and radish (*Raphanus sativus*) were sown. The soil in the vat was covered with a soil of 1 cm thickness containing seeds of weeds, i.e., barnyardgrass, large crabgrass, oats, common lambasquarters, and chickweed. When the weeds were grown to have 2.5-3.0 leaves, each of the compound Nos. 10 and 11, as well as the racemic compounds thereof (i.e., compound Nos. 3 and 1) were applied to the leaves and stems of the plants in the amount of 0.8, 0.4 or 0.2 g/a.

After 14 days from the application of the herbicide, the conditions of the growth of the weeds were observed, and the degree of growth inhibition was evaluated as in Example 10. The results are shown in Table 6 below.

TABLE 6

| Compound No. | Amount Treated (g/a) | soy-bean | beet | radish | barnyard-grass | large crabgrass | oats | common lambs-quaters | chick-weed |
| --- | --- | --- | --- | --- | --- | --- | --- | --- | --- |
| 10 | 0.8 | 1 | 1 | 1 | 5 | 5 | 5 | 1 | 1 |
|  | 0.4 | 1 | 1 | 1 | 5 | 5 | 5 | 1 | 1 |
|  | 0.2 | 1 | 1 | 1 | 5 | 5 | 5 | 1 | 1 |
| 11 | 0.8 | 1 | 1 | 1 | 5 | 5 | 5 | 1 | 1 |
|  | 0.4 | 1 | 1 | 1 | 5 | 5 | 5 | 1 | 1 |
|  | 0.2 | 1 | 1 | 1 | 5 | 5 | 5 | 1 | 1 |
| 3 | 0.8 | 1 | 1 | 1 | 4 | 4-5 | 5 | 1 | 1 |
|  | 0.4 | 1 | 1 | 1 | 3 | 3 | 4-5 | 1 | 1 |
|  | 0.2 | 1 | 1 | 1 | 3 | 2 | 3 | 1 | 1 |
| 1 | 0.8 | 1 | 1 | 1 | 4-5 | 4 | 5 | 1 | 1 |
|  | 0.4 | 1 | 1 | 1 | 3 | 3 | 4-5 | 1 | 1 |
|  | 0.2 | 1 | 1 | 1 | 2 | 2 | 3 | 1 | 1 |

As can be seen from Table 6, the compound Nos. 10 and 11, which are the R-enantiomers of compound Nos. 3 and 1, respectively, are still more effective in inhibiting the growth of the plants belonging to the Family Gramineae than their racemic compounds thereof.

EXAMPLE 14

Preparation of Compound No. 12

In 10 ml of dichloroethane, 0.35 g of tetrahydrofurfuryl alcohol was dissolved. To this solution, 1.05 g of 2-[4(3-chloro-5-trifluoromethyl-2-pyridyloxy)phenoxy]propionyl chloride in 5 ml of dichloroethane was added dropwise at room temperature. Then 0.3 ml of triethylamine was added to the solution and the resulting mixture was stirred at room temperature for 2 hours. To the thus obtained reaction mixture, water was added and the dichloroethane layer was separated, washed with water, dried over anhydrous magnesium sulfate and evaporated the solvent. The residue was purified by column chromatography (silica gel, eluant: chloroform) to obtain 0.97 g of the desired product (compound No. 12).

Refraction Index $n_D^{25} = 1.5214$.

$^1$H-NMR Spectrum (CDCl$_3$, δ ppm): 1.57 (3H, d), 1.73 (4H, mc), 3.63 (3H, mc), 4.03 (2H, s), 4.68 (1H, q), 6.83 (4H, mc), 7.80 (1H, d), 8.05 (1H, d).

EXAMPLE 15

Preparation of Compound No. 13

To 120 ml of acetonitrile, 8.76 g of 4-(5-trifluoromethyl-2-pyridyloxy)phenol, 8 g of α-chloropropionic acid tetrahydrofurfuryl ester and 5.7 g of anhydrous potassium carbonate were added and the resulting mixture was heated to reflux for 16 hours. After cooling the reaction mixture, inorganic materials were removed by filtration and the acetonitrile was evaporated. The residue was purified by column chromatography (silica gel, eluant: chloroform) to obtain 12.2 g of the desired product (compound No. 13).

Refraction Index $n_D^{25} = 1.5090$.

$^1$H-NMR Spectrum (CDCl$_3$, δ ppm): 1.57 (3H, d), 1.77 (4H, mc), 3.65 (3H, mc), 4.00 (2H, s), 4.67 (1H, q), 6.85 (4H, mc), 7.68 (1H, d), 7.83 (1H, d), 8.25 (1H, d).

EXAMPLE 16

Preparation of Compound No. 14

The same procedure as in Example 14 was repeated except that 2.18 g of 2-[4-(3-chloro-5-trifluoromethyl-2-pyridyloxy)phenoxy]propionyl chloride, 0.32 g of 3-hydroxytetrahydrofuran and 1.5 ml of triethylamine were used as the starting materials to obtain 0.7 g of the desired product (compound No. 14).

Refraction Index $n_D^{25} = 1.5212$.

$^1$H-NMR Spectrum (CDCl$_3$, δ ppm): 1.53 (3H, d), 1.95 (2H, mc), 3.68 (4H, mc), 4.65 (1H, q), 5.22 (1H, mc), 6.83 (4H, mc), 7.83 (1H, d), 8.09 (1H, d).

EXAMPLE 17

Preparation of Compound No. 15

The same procedure as in Example 14 was repeated except that 1.45 g of 2-[4-(3-chloro-5-trifluoromethyl-2-pyridyloxy)phenoxyl]propionyl chloride, 0.67 g of furfuryl alcohol and 0.8 ml of triethylamine were used as the starting materials to obtain 1.15 g of the desired product (compound No. 15).

Refraction Index $n_D^{25} = 1.5255$.

$^1$H-NMR Spectrum (CDCl$_3$, δ ppm): 1.54 (3H, d), 4.60 (1H, q), 4.98 (2H, s), 6.18 (2H, m), 6.75 (4H, mc), 7.22 (1H, m), 7.78 (1H, d), 8.04 (1H, d).

EXAMPLE 18

Preparation of Compound No. 16

The same procedure as in Example 14 was repeated except that 1.09 g of 2-[4-(3-chloro-5-trifluoromethyl-2-pyridyloxy)phenoxy]propionyl chloride, 0.4 g of 2-hydroxymethyltetrahydropyran and 0.4 ml of triethylamine were used as the starting materials to obtain 1.05 g of the desired product (compound No. 16).

Refraction Index $n_D^{25} = 1.5198$.

$^1$H-NMR Spectrum (CDCl$_3$, δ ppm): 1.57 (3H, d), 1.38 (6H, mc), 1.65 (2H, mc), 3.78 (1H, mc), 3.98 (2H, d), 4.63 (1H, q), 6.80 (4H, mc), 7.80 (1H, d), 8.05 (1H, d).

EXAMPLE 19

Preparation of Compound No. 17

The same procedure as in Example 14 was repeated except that 1.09 g of 2-[4-(3-chloro-5-trifluoromethyl-2-pyridyloxy)phenoxy]propionyl chloride, 0.42 g of 5-methyl tetrahydrofurfuryl alcohol and 0.4 ml of triethylamine were used as the starting materials to obtain 1.18 g of the desired product (compound No. 17).

Refraction Index $n_D^{25} = 1.5141$.

$^1$H-NMR Spectrum (CDCl$_3$, δ ppm): 1.12 (3H, d), 1.55 (3H, d), 1.82 (4H, mc), 4.00 (4H, mc), 4.00 (2H, s), 4.63 (1H, q), 6.77 (4H, mc), 7.78 (1H, d), 8.04 (1H, d).

EXAMPLE 20

Test for Evaluation of Effectiveness of Growth Inhibition by Treatment of Leaves and Stems The effectiveness of compound Nos. 12–17 was evaluated as in Example 10 except that the amount of the compounds used was 64, 16, 4 or 1 g/ha. Further, for the purpose of comparison, conventional herbicide, i.e., 2-[4-(5-trifluoromethyl-2-pyridyloxy)phenoxy]propionic acid butyl ester (Compound [A]), 2-[4-(2,4-dichlorophenoxy)phenoxy]propionic acid tetrahydrofurfuryl ester (Compound [B]), 2-[4-(2-chloro-4-trifluormethylphenyl)phenoxy]propionic acid tetrahydrofurfuryl ester (Compound [C]) or 2-[4(3,5-dichloro-2-pyridyloxy)phenoxy]propionic acid ethyl ester (Compound [D])

was also applied. The results are shown in Table 7 below.

TABLE 7

| Compound No. | Amount Treated (g/ha) | soybean | rice | wheat | oats | corn | large crabgrass | barnyardgrass | chickweed | common lambsquaters | polygonum |
|---|---|---|---|---|---|---|---|---|---|---|---|
| 12 | 64 | 1 | 5 | 5 | 5 | 5 | 5 | 5 | 1 | 1 | 1 |
|  | 16 | 1 | 5 | 5 | 5 | 5 | 5 | 5 | 1 | 1 | 1 |
|  | 4 | 1 | 4–5 | 5 | 5 | 5 | 5 | 5 | 1 | 1 | 1 |
|  | 1 | 1 | 4 | 4–5 | 5 | 5 | 4–5 | 5 | 1 | 1 | 1 |
| 13 | 64 | 1 | 5 | 5 | 5 | 5 | 5 | 5 | 1 | 1 | 1 |
|  | 16 | 1 | 4 | 5 | 5 | 5 | 5 | 5 | 1 | 1 | 1 |
|  | 4 | 1 | 4 | 5 | 5 | 5 | 4 | 4–5 | 1 | 1 | 1 |
|  | 1 | 1 | 3 | 2 | 3 | 3 | 3 | 3 | 1 | 1 | 1 |
| 14 | 64 | 1 | 5 | 5 | 5 | 5 | 5 | 5 | 1 | 1 | 1 |
|  | 16 | 1 | 4–5 | 5 | 5 | 5 | 5 | 5 | 1 | 1 | 1 |
|  | 4 | 1 | 3 | 4 | 3 | 2 | 2 | 2 | 1 | 1 | 1 |
|  | 1 | 1 | 1 | 3 | 1 | 1 | 1 | 1 | 1 | 1 | 1 |
| 15 | 64 | 1 | 5 | 5 | 5 | 5 | 5 | 5 | 1 | 1 | 1 |
|  | 16 | 1 | 5 | 5 | 5 | 5 | 5 | 5 | 1 | 1 | 1 |
|  | 4 | 1 | 3 | 4 | 5 | 4 | 4 | 5 | 1 | 1 | 1 |
|  | 1 | 1 | 1 | 2 | 1 | 1 | 1 | 1 | 1 | 1 | 1 |
| 16 | 64 | 1 | 5 | 5 | 5 | 5 | 5 | 5 | 1 | 1 | 1 |
|  | 16 | 1 | 5 | 5 | 5 | 5 | 5 | 5 | 1 | 1 | 1 |
|  | 4 | 1 | 4–5 | 5 | 5 | 5 | 5 | 5 | 1 | 1 | 1 |
|  | 1 | 1 | 4 | 4–5 | 5 | 4 | 4 | 5 | 1 | 1 | 1 |
| 17 | 64 | 1 | 5 | 5 | 5 | 5 | 5 | 5 | 1 | 1 | 1 |
|  | 16 | 1 | 4–5 | 5 | 5 | 5 | 5 | 5 | 1 | 1 | 1 |
|  | 4 | 1 | 4–5 | 4–5 | 5 | 5 | 5 | 5 | 1 | 1 | 1 |
|  | 1 | 1 | 4 | 4–5 | 5 | 5 | 5 | 5 | 1 | 1 | 1 |
| [A] | 64 | 1 | 5 | 5 | 5 | 5 | 5 | 5 | 1 | 1 | 1 |
|  | 16 | 1 | 4–5 | 5 | 5 | 5 | 5 | 5 | 1 | 1 | 1 |
|  | 4 | 1 | 1 | 2 | 3 | 3 | 3 | 4 | 1 | 1 | 1 |
|  | 1 | 1 | 1 | 1 | 1 | 1 | 1 | 1 | 1 | 1 | 1 |
| [B] | 64 | 1 | 3 | 1 | 2 | 1 | 2 | 2 | 1 | 1 | 1 |
|  | 16 | 1 | 1 | 1 | 1 | 1 | 1 | 1 | 1 | 1 | 1 |
|  | 4 | 1 | 1 | 1 | 1 | 1 | 1 | 1 | 1 | 1 | 1 |
|  | 1 | 1 | 1 | 1 | 1 | 1 | 1 | 1 | 1 | 1 | 1 |
| [C] | 64 | 1 | 4–5 | 4 | 4–5 | 4 | 4 | 5 | 1 | 1 | 1 |
|  | 16 | 1 | 2 | 2 | 4 | 2 | 4 | 4–5 | 1 | 1 | 1 |
|  | 4 | 1 | 1 | 1 | 1 | 1 | 1 | 4–5 | 1 | 1 | 1 |
|  | 1 | 1 | 1 | 1 | 1 | 1 | 1 | 1 | 1 | 1 | 1 |
| [D] | 64 | 1 | 1 | 1 | 2 | 1 | 2 | 2 | 1 | 1 | 1 |
|  | 16 | 1 | 1 | 1 | 1 | 1 | 1 | 1 | 1 | 1 | 1 |
|  | 4 | 1 | 1 | 1 | 1 | 1 | 1 | 1 | 1 | 1 | 1 |
|  | 1 | 1 | 1 | 1 | 1 | 1 | 1 | 1 | 1 | 1 | 1 |

It can be seen from Table 7 that the compound of the present invention is more effective for inhibiting the growth of the plants belonging to the Family Gramineae than the conventional herbicides and harmless to the broadleaved plants.

EXAMPLE 21

Field Test

On plowed and pulverized field, seeds of soybean, rapeseed and beet were sown and covered with soil. Weeds belonging to the Family Gramineae, i.e., green foxtail (*Setaria viridis*), barnyardgrass and Johnson grass (*Sorghum halepense*) and broadleaved weeds, i.e. large crabgrass, common lambsquarters and chickweed grew naturally.

The compound No. 12 was formulated to an emulsifiable concentrate in accordance with the above-mentioned Composition 1.

When the weeds belonging to the Family Gramineae grew to have 4.0–5.0 leaves or 6.0–7.0 leaves, the composition containing the compound No. 12 was applied to the weeds in the amount of 0.6, 0.3 or 1.15 kg/ha. For comparison, compound [A] was also applied in the same manner. After 21 days from the application of the compositions, growth conditions of the plants were observed and evaluated as in Example 10. The results are shown in Tables 8 and 9 below.

obtain 0.97 g of the desired product (compound No. 18 (R-enantiomer of compound 12)).

Specific Rotation $[\alpha]_D^{20} = +33.5°$ (c=1.07, CHCl$_3$).

$^1$N-NMR Spectrum (CDCl$_3$, ppm): 1.66 (3H, d), 1.90 (4H, mc), 3.80 (3H, t), 4.14 (2H, d), 4.78 (1H, t), 6.97 (4H, d), 7.90 (1H, d), 8.18 (1H, d).

EXAMPLE 23

Test for Evaluation of Effectiveness in Growth Inhibition by Treatment of Soil In a plastic vat sized 22 cm×16 cm, field soil was packed and seeds of soybean, beet, radish and oats were sown. Field soil containing seeds of weeds shown in Table 10 below with a thickness of 1 cm was laid on the soil in the vat. When the weeds belonging to the Family Gramineae grew to have 2.4–3.0 leaves, compound Nos. 18 and 12 was uniformly applied to the soil. After 14 days from the application, grown conditions of the plants were observed and evaluated in accordance with the following criteria:

TABLE 8

| Compound No. | Amount Treated (kg/ha) | soy-bean | rape-seed | beet | *Setaria viridis* | barnyard-grass | Johnson grass | large crabgrass | common lambs-quaters | chick-weed |
|---|---|---|---|---|---|---|---|---|---|---|
| 12 | 0.6 | 1 | 1 | 1 | 5 | 5 | 5 | 5 | 1 | 1 |
|  | 0.3 | 1 | 1 | 1 | 5 | 5 | 5 | 5 | 1 | 1 |
|  | 0.15 | 1 | 1 | 1 | 5 | 5 | 5 | 5 | 1 | 1 |
| [A] | 0.6 | 1 | 1 | 1 | 5 | 4–5 | 5 | 4 | 1 | 1 |
|  | 0.3 | 1 | 1 | 1 | 3 | 4 | 4 | 2 | 1 | 1 |
|  | 0.15 | 1 | 1 | 1 | 2 | 3 | 3 | 1 | 1 | 1 |

TABLE 9

| Compound No. | Amount Treated (kg/ha) | soy-bean | rape-seed | beet | *Setaria viridis* | barnyard-grass | Johnson grass | large crabgrass | common lambs-quaters | chick-weed |
|---|---|---|---|---|---|---|---|---|---|---|
| 12 | 0.6 | 1 | 1 | 1 | 5 | 5 | 5 | 5 | 1 | 1 |
|  | 0.3 | 1 | 1 | 1 | 5 | 5 | 5 | 5 | 1 | 1 |
|  | 0.15 | 1 | 1 | 1 | 5 | 5 | 5 | 5 | 1 | 1 |
| [A] | 0.6 | 1 | 1 | 1 | 4 | 4 | 4 | 3 | 1 | 1 |
|  | 0.3 | 1 | 1 | 1 | 3 | 2 | 3 | 2 | 1 | 1 |
|  | 0.15 | 1 | 1 | 1 | 1 | 1 | 1 | 1 | 1 | 1 |

As can be seen from Tables 8 and 9, the compound No. 12 of the present invention is more effective in inhibiting the growth of the weeds belonging to the Family Gramineae than the conventional compound [A].

EXAMPLE 22

Preparation of Compound No. 18

The same procedure as in Example 11 was repeated except that 1.17 g of R-(+)-2-[4-(3-chloro-5-trifluoromethyl-2-pyridyloxy)phenoxy]propionyl chloride, 0.38 g of tetrahydrofurfuryl alcohol and 0.37 g of triethylamine were used as the starting materials to

| Rank | % Inhibition |
|---|---|
| 10 | 100 |
| 9 | 99–90 |
| 8 | 89–80 |
| 7 | 79–70 |
| 6 | 69–60 |
| 5 | 59–50 |
| 4 | 49–40 |
| 3 | 39–30 |
| 2 | 29–20 |
| 1 | 19–0 |

For the purposes of comparison, above-mentioned compound [A] was also tested in the same manner. The results are shown in Table 10.

TABLE 10

| Compound No. | Amount Treated (g/ha) | soy-bean | beet | radish | oats | large crabgrass | barnyard-grass | Johnson grass | chick-weed | common lambs-quaters |
|---|---|---|---|---|---|---|---|---|---|---|
| 18 | 15 | 1 | 1 | 1 | 10 | 10 | 10 | 10 | 1 | 1 |
|  | 7.5 | 1 | 1 | 1 | 10 | 10 | 10 | 10 | 1 | 1 |
|  | 3.75 | 1 | 1 | 1 | 10 | 10 | 10 | 10 | 1 | 1 |
|  | 1.875 | 1 | 1 | 1 | 10 | 10 | 10 | 8 | 1 | 1 |
| 12 | 15 | 1 | 1 | 1 | 10 | 10 | 10 | 10 | 1 | 1 |
|  | 7.5 | 1 | 1 | 1 | 10 | 9 | 10 | 10 | 1 | 1 |
|  | 3.75 | 1 | 1 | 1 | 7 | 8 | 10 | 6 | 1 | 1 |

TABLE 10-continued

| Compound No. | Amount Treated (g/ha) | soy-bean | beet | radish | oats | large crabgrass | barnyard-grass | Johnson grass | chick-weed | common lambs-quaters |
|---|---|---|---|---|---|---|---|---|---|---|
|  | 1.875 | 1 | 1 | 1 | 2 | 4 | 6 | 3 | 1 | 1 |
| [A] | 15 | 1 | 1 | 1 | 6 | 7 | 9 | 8 | 1 | 1 |
|  | 7.5 | 1 | 1 | 1 | 3 | 4 | 6 | 3 | 1 | 1 |
|  | 3.75 | 1 | 1 | 1 | 1 | 1 | 2 | 1 | 1 | 1 |
|  | 1.875 | 1 | 1 | 1 | 1 | 1 | 1 | 1 | 1 | 1 |

EXAMPLE 24

Preparation of Compound No. 19

To 50 ml of acetonitrile, 1.02 g of 4(3,5-dichloro-2-pyridyloxy)-phenol, 0.88 g of α-chloropropionic acid 1-3-methyl-1,2,4-oxadiazole-5-yl)ethyl ester and 0.69 g of anhydrous potassium carbonate were added and the resulting mixture was heated to reflux for 16 hours under stirring. After cooling the reaction mixture, inorganic materials were removed by filtration and acetonitrile was evaporated. The residue was purified by column chromatography [silica gel, eluant: benzene/ethyl acetate=10/1 (v/v)] to obtain 0.56 g of the desired product (compound No. 19).

Refraction Index $n_D^{25}=1.5541$.

$^1$H-NMR Spectrum (CDCl$_3$, δ ppm): 1.65 (3H, d), 1.68 (3H, d), 2.36 (3H, s), 4.82 (1H, q), 6.05 (1H, q), 6.93 (4H, mc), 7.65 (1H, d), 7.8 4 (1H, d).

EXAMPLE 25

Preparation of Compound No. 20

The same procedure as in Example 24 was repeated except that 0.8 g of 4-(6-chloro-quinoxaline-2-yloxy)-phenol, 0.65 g of α-chloropropionic acid 1-(3-methyl-1,2,4-oxadiazole-5-yl) ethyl ester and 0.45 g of anhydrous potassium carbonate were used as the starting materials to obtain 0.85 g of the desired product (compound No. 20).

Refraction Index $n_D^{25}=1.5823$.

$^1$H-NMR Spectrum (CDCl$_3$, δ ppm): 1.70 (6H, d), 2.37 (3H, s), 4.90 (1H, q), 6.12 (1H, q), 7.02 (4H, mc), 7.52 (2H, m), 7.92 (1H, m), 8.53 (1H, s).

EXAMPLE 26

Preparation of Compound No. 21

The same procedure as in Example 24 was repeated except that 1.0 g of 4-(6-chloro-quinoxaline-2-yloxy)-phenol, 0.85 g of α-chloropropionic acid tetrahyrofurfuryl ester and 0.61 g of anhydrous potassium carbonate were used as the starting materials to obtain 1.46 g of the desired product (compound No. 21).

m.p.: 47°–49° C.

$^1$H-NMR Spectrum (CDCl$_3$, δ ppm): 1.64 (3H, d), 1.83 (4H, mc), 3.78 (3H, mc), 4.17 (2H, s), 4.82 (1H, q), 6.98 (4H, mc), 7.47(2H, m), 7.88 (1H, m), 8.53 (1H, s).

EXAMPLE 27

Preparation of Compound No. 22

The same procedure as in Example 24 was repeated except that 0.9 g of 4-(3,5-dichloro-2-pyridyloxy)-phenol, 0.77 g of α-chloropropionic acid tetrahydrofurfuryl ester and 0.55 g of anhydrous potassium carbonate were used as the starting materials to obtain 1.09 g of the desired product (compound No. 22).

Refraction Index $n_D^{25}=1.5620$.

$^1$H-NMR Spectrum (CDCl$_3$, δ ppm): 1.48 (3H, d), 1.66 (4H, mc), 3.66 (3H, mc), 4.05 (2H, s), 4.69 (1H, q), 6.85 (4H, mc), 7.58 (1H, d), 7.78 (1H, d).

EXAMPLE 28

Test for Evaluation of Effectiveness in Growth Inhibition by Treatment of Leaves and Stems Using the compound Nos. 19–22, the similar test as in Example 10 was carried out. For the purpose of comparison, 2-[4-(5-cyano-pyridyl-2-oxy)phenoxy]propionic acid 1(3-methyl-1,2,4-oxadiazole-5-yl) ethyl ester (compound [E]) and 2-[4-(5-cyano-pyridyl-2-oxy)-phenoxy]propionic acid tetrahydrofurfuryl ester (compound [F]) were also tested. The results are shown in Table 11 below.

TABLE 11

| Compound No. | Amount Treated (g/ha) | soy-bean | rice | wheat | oats | corn | large crabgrass | barnyard-grass | Johnson grass | broad leaved weeds |
|---|---|---|---|---|---|---|---|---|---|---|
| 19 | 500 | 1 | 5 | 4–5 | 5 | 5 | 5 | 5 | 5 | 1 |
|  | 125 | 1 | 3 | 4 | 5 | 5 | 5 | 5 | 5 | 1 |
|  | 31.25 | 1 | 3 | 2 | 4 | 3 | 3 | 4–5 | 5 | 1 |
|  | 7.8 | 1 | 1 | 1 | 4 | 3 | 2 | 2 | 3 | 1 |
| 20 | 500 | 1 | 5 | 5 | 5 | 5 | 5 | 5 | 5 | 1 |
|  | 125 | 1 | 5 | 5 | 5 | 5 | 5 | 5 | 5 | 1 |
|  | 31.25 | 1 | 5 | 5 | 5 | 5 | 5 | 5 | 5 | 1 |
|  | 7.8 | 1 | 4–5 | 5 | 5 | 5 | 4–5 | 4–5 | 5 | 1 |
| 21 | 500 | 1 | 5 | 5 | 5 | 5 | 5 | 5 | 5 | 1 |
|  | 125 | 1 | 5 | 5 | 5 | 5 | 5 | 5 | 5 | 1 |
|  | 31.25 | 1 | 5 | 5 | 5 | 5 | 5 | 5 | 5 | 1 |
|  | 7.8 | 1 | 4–5 | 5 | 4 | 5 | 5 | 5 | 5 | 1 |
| 22 | 500 | 1 | 5 | 5 | 5 | 5 | 5 | 5 | 5 | 1 |
|  | 125 | 1 | 4 | 4–5 | 5 | 5 | 5 | 5 | 5 | 1 |
|  | 31.25 | 1 | 4 | 3 | 5 | 5 | 5 | 5 | 5 | 1 |
|  | 7.8 | 1 | 3 | 2 | 5 | 5 | 5 | 5 | 5 | 1 |
| [E] | 500 | 1 | 1 | 1 | 1 | 1 | 1 | 1 | 1 | 1 |
|  | 125 | 1 | 1 | 1 | 1 | 1 | 1 | 1 | 1 | 1 |
|  | 31.25 | 1 | 1 | 1 | 1 | 1 | 1 | 1 | 1 | 1 |

TABLE 11-continued

| Compound No. | Amount Treated (g/ha) | soy-bean | rice | wheat | oats | corn | large crabgrass | barnyard-grass | Johnson grass | broad leaved weeds |
| --- | --- | --- | --- | --- | --- | --- | --- | --- | --- | --- |
|  | 7.8 | 1 | 1 | 1 | 1 | 1 | 1 | 1 | 1 | 1 |
| [F] | 500 | 1 | 1 | 1 | 1 | 2 | 2 | 2 | 2 | 1 |
|  | 125 | 1 | 1 | 1 | 1 | 1 | 1 | 1 | 1 | 1 |
|  | 31.25 | 1 | 1 | 1 | 1 | 1 | 1 | 1 | 1 | 1 |
|  | 7.8 | 1 | 1 | 1 | 1 | 1 | 1 | 1 | 1 | 1 |

As can be seen from Table 11, the compound Nos. 19–22 of the present invention are much more effective than the structurally similar comparative compounds in growth inhibition of the plants belonging to the Family Gramineae.

EXAMPLE 29

Test for Evaluation of Effectiveness in Growth Inhibition by Treatment of Soil

The same procedure as in Example 28 was repeated except that the compound Nos. 19 and 21 were applied to the soil on the next day of sowing. The results are shown in Table 12 below.

TABLE 12

| Compound No. | Amount Treated (g/ha) | soy-bean | rice | wheat | oats | corn | large crabgrass | barnyard-grass | Johnson grass | broad leaved weeds |
| --- | --- | --- | --- | --- | --- | --- | --- | --- | --- | --- |
| 19 | 1000 | 1 | 4 | 2 | 1 | 1 | 5 | 5 | 5 | 1 |
|  | 250 | 1 | 1 | 1 | 1 | 1 | 3 | 4 | 4 | 1 |
|  | 62.5 | 1 | 1 | 1 | 1 | 1 | 2 | 2 | 1 | 1 |
| 21 | 1000 | 1 | 4 | 3 | 2 | 3 | 4 | 5 | 5 | 1 |
|  | 250 | 1 | 1 | 1 | 1 | 2 | 4 | 4 | 5 | 1 |
|  | 62.5 | 1 | 1 | 1 | 1 | 1 | 3 | 3 | 2 | 1 |
| [E] | 1000 | 1 | 1 | 1 | 1 | 1 | 1 | 1 | 1 | 1 |
|  | 250 | 1 | 1 | 1 | 1 | 1 | 1 | 1 | 1 | 1 |
|  | 62.5 | 1 | 1 | 1 | 1 | 1 | 1 | 1 | 1 | 1 |
| [F] | 1000 | 1 | 1 | 1 | 1 | 1 | 1 | 1 | 1 | 1 |
|  | 250 | 1 | 1 | 1 | 1 | 1 | 1 | 1 | 1 | 1 |
|  | 62.5 | 1 | 1 | 1 | 1 | 1 | 1 | 1 | 1 | 1 |

As can be seen from Table 12, the compound Nos. 19 and 21 of the present invention are much more effective than the structurally similar comparative compounds in growth inhibition of the plants belonging to the Family Gramineae.

We claim:

1. A phenoxy propionic acid ester derivative of the formula [ii]:

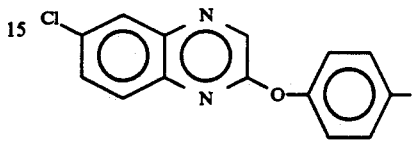

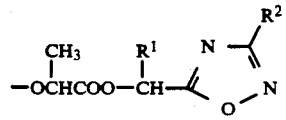

wherein $R^1$ is H or $CH_3$, $R^2$ is H or $C_1$–$C_4$ alkyl group.

2. A herbicide composition comprising a herbicidally effective amount of the phenoxy propionic acid ester derivative of claim 1 in an agriculturally acceptable carrier.

* * * * *